United States Patent [19]

Kalopissis et al.

[11] 4,067,869
[45] Jan. 10, 1978

[54] 3-AMINO-2-AZA BENZOQUINONE DIIMINES

[75] Inventors: Gregoire Kalopissis, Paris; Andree Bugaut, Boulogne-sur-Seine; Francoise Estradier, Paris, all of France

[73] Assignee: L'Oreal, Paris, France

[21] Appl. No.: 727,480

[22] Filed: Sept. 28, 1976

Related U.S. Application Data

[60] Division of Ser. No. 576,784, May 12, 1975, Pat. No. 3,997,546, which is a division of Ser. No. 387,612, Aug. 13, 1973, Pat. No. 3,893,802, which is a continuation-in-part of Ser. No. 131,458, April 5, 1971, abandoned.

[30] Foreign Application Priority Data

Apr. 10, 1970 Luxembourg .......................... 60702

[51] Int. Cl.$^2$ ............................................ C07D 213/74
[52] U.S. Cl. ........................ 260/270 PY; 260/294.8 R; 260/295.5 A

[58] Field of Search ................ 260/295.5 A, 270 PY, 260/294.8 R

[56] References Cited

U.S. PATENT DOCUMENTS 3,997,546  12/1976  Kalopissis et al. ............... 260/295 S

OTHER PUBLICATIONS

Corbett, "Chemical Abstracts", vol. 71, abst. No. 103,156a, (1969).
Kalopissis et al., Chemical Abstracts, vol. 76, abst. No. 73756e (1972), (abst. of German Offen 2,117,363 published Oct. 28, 1971).

*Primary Examiner*—Natalie Trousof
*Assistant Examiner*—R. W. Ramsuer
*Attorney, Agent, or Firm*—Cushman, Darby & Cushman

[57] ABSTRACT

A process for producing indamine by condensing 2,6-diamino pyridine on a paraphenylene diamine or a benzoquinone diimine or a paranitroso N,N-dialkyl aniline. The resulting indamine can be incorporated into a dye composition for keratinic fibers, especially human hair.

5 Claims, No Drawings

3-AMINO-2-AZA BENZOQUINONE DIIMINES

This application is a division of application Ser. No. 576,784, filed May 12, 1975, now U.S. Pat. No. 3,997,546, which in turn is a division of Ser. No. 387,612, filed Aug. 13, 1973, now U.S. Pat. No. 3,893,802, which in turn is a CIP of Ser. No. 131,458, filed Apr. 5, 1971, now abandoned.

The present invention relates to new indamines having the formula

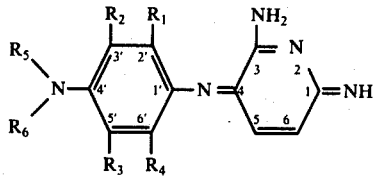

wherein $R_1$, $R_2$, $R_3$ and $R_4$ each represent a member selected from the group consisting of hydrogen, halogen, lower alkyl having 1–4 carbon atoms and lower alkoxy having 1–4 carbon atoms, and $R_5$ and $R_6$ are either both hydrogen atoms, or both substituted or nonsubstituted lower alkyl radicals which may be identical or different, such as methyl, ethyl, butyl, hydroxyalkyl, carbamyl alkyl, piperidinoalkyl, or acylaminoalkyl radicals. Because the indamines of Formula I in the form of their free bases are generally more difficult to isolate and preserve than their salts, which are readily isolated and preserved, the present invention also relates to salts of the compounds of Formula I with organic or mineral acids, especially their acetates, tartrates, aryl sulfonates, hydrochlorides, hydrobromides, persulfates, perchlorates or double chlorides of zinc, as well as indamines that yield these compounds with zinc chloride.

The indamines of the present invention can be prepared by condensing 2,6-diaminopyridine on a paraphenylenediamine having the formula:

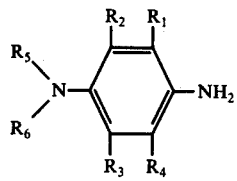

wherein $R_1$, $R_2$, $R_3$, $R_4$, $R_5$ and $R_6$ have the meanings given above, said condensation being effected in an aqueous medium, an aqueous alcoholic medium or an aqueous acetonic medium in the presence of an oxidizing agent. When desired, the reaction can also involve the conversion of the resulting indamine into a salt thereof. When an aqueous alcohol medium is employed, the alcohol used can be, for instance, a lower alkanol having 1–4 carbon atoms, the alkanol being present in amounts of about 75 to 10 percent by weight of the total aqueous alcohol medium. When an aqueous acetonic medium is employed, acetone can comprise between about 75 to 10 weight percent of the medium. The condensation reaction is generally carried out at atmospheric pressure and at a temperature ranging from about 0° to 50° C. Generally the paraphenylene diamine and 2,6-diaminopyridine are employed in essentially equimolar amounts.

The oxidizing agent employed in the condensation reaction is advantageously hydrogen peroxide or a water-soluble persalt, such as an alkali persulfate or ammonium persulfate which permits ready recovery of the indamine of Formula I as an insoluble persulfate. Generally the oxidizing agent will be present in amounts ranging from about one or two times the theoretical amount to make the quinone diimine.

When the oxidizing agent used is hydrogen peroxide and when the indamine salt desired is only slightly soluble in water, the condensation of 2,6-diaminopyridine on paraphenylene diamine of Formula (II) can be followed by addition to the reaction mixture of either an acid corresponding to the desired salt, or a salt of this acid which is more soluble in water than is the desired indamine salt, for example, ammonium persulfate.

It has also been noted that even in the case where it is desired to prepare an indamine persulfate, it is often advantageous to proceed in two stages, the first stage comprising oxidizing the mixture of 2,6-diaminopyridine and paraphenylene diamine of Formula II by means of hydrogen peroxide and the second stage comprising adding the appropriate persalt to the resulting reaction mixture.

When it is desired to obtain indamine salts that are very readily soluble in water, it is necessary to operate in two stages. The first stage comprises preparing a relatively insoluble and hence isolatable indamine salt, e.g. a persulfate or a hydrochloride, and treating this salt in a second stage with an alkaline solution from which the indamine of Formula I is extracted by means of a suitable solvent, said indamine being then converted to the desired salt by addition of the corresponding acid to the solvent phase. This way of proceeding applies for cases in which it is desired to prepare, e.g. an acetate, a tartrate or a paratoluene sulfate.

Representative paraphenylene diamines that can be used in the process of this invention include, for example, paraphenylene diamine, paratoluylene diamine, 2,5-diaminoanisole, 2,5-diamino-chlorobenzene, 2-methoxy 5-methyl paraphenylene diamine, 2,6-dimethyl 3-methoxy paraphenylene diamine, 1,4-diamino-durene, and N,N-dimethylparaphenylene diamine.

Those indamine salts of the present invention which are characterized by the fact that $R_5$ and $R_6$ are both hydrogen, and at least two of the radicals $R_1$, $R_2$, $R_3$ and $R_4$ are not hydrogen atoms, can, on the other hand, be prepared by condensing 2,6-diaminopyridine on a benzoquinone diimine having the formula

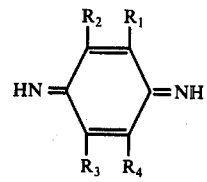

wherein $R_1$, $R_2$, $R_3$ and $R_4$ have the meanings indicated above, with the proviso that at least two of these radicals do not represent hydrogen, the said condensation being effected either in an aqueous medium, or in an inert solvent such as methyl isobutylketone, acetone, dioxane, ether or benzene, in the presence of the acid that corresponds to the desired salt. Representative acids included organic acids such as acetic, tartaric, oxalic and paratoluene sulfonic acid, and mineral acids such as perchloric acid.

Representative benzoquinone diimines usefully employed in the present invention include 2-methyl 5- methoxy benzoquinone diimine, 2-methoxy 3,5-dimethyl benzoquinone diimine and 2,5-dimethoxy benzoquinone diimine, the benzoquinone diimines and 2,6-diaminopyridine being generally used in equimolar quantities. The reaction is generally carried out at ambient temperature and pressure.

Those indamine salts of the present invention which are characterized by the fact that $R_5$ and $R_6$ are both substituted or non-substituted alkyl radicals can be prepared by condensing 2,6-diaminopyridine on a paranitroso N,N dialkyl aniline having the formula

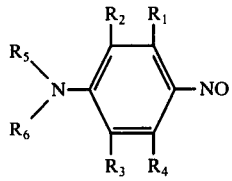

wherein $R_1$, $R_2$, $R_3$ and $R_4$ have the meanings given above and wherein $R_5$ and $R_6$ are both alkyl or substituted alkyl radicals as indicated above, or on salts of these nitroso derivatives, such as hydrochlorides or hydrobromides, the reaction being effected in an aqueous medium at a temperature between 30 and 60° C or in an alcohol medium, for instance, a lower alkanol having 1-4 carbon atoms such as ethyl alcohol, especially when it is desired to isolate indamines (I) as double chlorides of zinc.

The indamines of the present invention are dyes whose solubility in water and in alcohol is quite acceptable, their solubility being generally sufficient to effect capillary dyeing, especially in a pH range of 3 to 10.

Accordingly, the present invention also relates to a new product of manufacture comprising a dye composition for dyeing keratinic fibers, especially human hair, containing in solution at least one indamine of Formula I.

The dye compositions of the present invention can include the indamines of Formula I alone, in which case they produce on white hair, shades that range from blue to green, at the end of extremely short application periods, in the order of about 3 minutes, at ambient temperature. Because of the great dyeing power of the indamines of this invention, their concentration in a dye composition can be extremely low, for instance, about 0.002% by weight of the composition. However, this concentration can vary from about 0.002 to 1% by weight.

Alternatively, the dye compositions of the present invention can include other direct dyes, e.g. azo dyes, anthraquinone dyes and nitro benzene dyes as well as oxazines, azines and indoanilines, indophenols, or indamines other than those of Formula I.

The dye compositions of the present invention impart to the hair to which they are applied shades which are rich in highlights. Further, these dye compositions can mask the red of chestnut red or brownish red hair, even when the hair in question is very dark.

The dye compositions of this invention are generally in the form of aqueous or aqueous alcohol solution which can be readily prepared by dissolving one or more of the indamines of Formula I with or without other direct dyes and the composition can also include other conventional adjuvants such as thickeners, and thus be in the form of creams and gels, wetting agents, dispersants, swelling agents, penetrating agents, emollients or perfumes. Moreover, the compositions can be packaged under pressure with conventional propellants in aerosol containers.

The pH of the dye compositions of the present invention can vary within wide limits. However, the pH generally ranges between 3.5 and 10 and preferably between 5 and 9.

The dyeing of keratinic fibers, especially human hair, using the dye compositions of the present invention is effected in the usual way by applying the composition to the fibers that are to be dyed, permitting the composition to remain in contact therewith for a time that ranges from about 3 to 30 minutes and rinsing the thus treated fibers. If desired, the rinsed fibers can be subsequently washed and dried.

In another embodiment of the present invention, the novel indamines can be employed in the production of capillary hair setting lotions. These lotions comprise an aqueous alcohol solution of at least one cosmetic resin and at least one indamine of Formula I, or one of its salts, or a double chloride of zinc and indamine, as defined above. The amount of indamine present in the hair setting lotion of the present invention can also be extremely low. Such an amount generally ranges between about 0.002 to 1% by weight of the total hair setting lotion composition.

Representative cosmetic resins that can be employed in the hair setting lotion composition of the present invention include, for instance, polyvinylpyrrolidone, having a molecular weight ranging from about 10,000 to 70,000, copolymer of crotonic acid and vinyl acetate, copolymer of vinylpyrrolidone and vinyl acetate wherein the ratio of PVP to PVA ranges between 50-70:50-30, copolymer of maleic anhydride and butyl-vinyl ether and the like. These resins are utilized in a proportion of about 1 to 3% by weight.

The alcohols that are suitable for the preparation of the hair setting lotions of the invention are low molecular weight alkanols, preferably ethanol or isopropanol, which are present in amounts of about 20 to 50% by weight of the total hair setting lotion composition. The pH of the hair setting lotion of this invention can range from about 3 to 10, and preferably between about 4 and 9.

Hair setting lotions of the present invention that contain as dyes only indamines of the present invention are tinting compositions which made it possible to impart an extremely lustrous sheen to chestnut-reddish or brownish-red hair, thereby masking the red thereof.

However, the hair setting lotions of this invention can also include other direct dyes such as azo dyes, anthraquinone dyes, nitrobenzene dyes, indoanilines, indophenols, or other indamines, oxazines or azines. These lotions are used in the customary way by applying the same to wet hair which has been previously washed and rinsed, followed by rolling up and drying of the hair.

The following examples illustrate the various aspects of the present invention.

EXAMPLE 1

N-[(4'-amino 2'-methoxy 5'-methyl)phenyl] 3-amino 2-aza benzoquinone diimine monoacetate is prepared as follows:

There is dissolved at ambient temperature 0.04 mole 3-methoxy 6-methyl benzoquinone diimine (6 g) in 120 cc methylisobutylketone, and there is immediately added to this solution 0.04 mole (4.3 g) 2,6-diaminopyridine in 120 cc dioxane to which 6 cc acetic acid have been added. The reaction mixture is then immediately filtered, yielding 5.5 g of the desired indamine as the monoacetate. The product which is obtained and which is chromatographically pure, melts with decomposition between 190° and 193°.

Molecular weight calculated for $C_{15}H_{19}N_5O_3$ ... 317
Molecular weight measured with a "Mechrolab" osmometer ... 310
Molecular weight found by potentiometric measurement effected with perchloric acid in acetic medium ... 322

| Analysis | Calculated for $C_{15}H_{19}N_5O_3$ | Found | |
|---|---|---|---|
| C% | 56.78 | 56.15 | 56.22 |
| H% | 5.99 | 6.09 | 5.85 |
| N% | 22.08 | 21.67 | 21.80 |

EXAMPLE 2

N-[(4'-amino 2'-methoxy 3',5'-dimethyl)phenyl] 3-amino 2-aza benzoquinone diimine monoacetate is prepared as follows:

There is dissolved, at ambient temperature, 0.05 mole (8.2 g) 3-methoxy 2,6-dimethyl benzoquinone diimine in 100 cc methylisobutylketone, and there is immediately added to this resulting solution 0.05 mole (5.45 g) 2,6-diamino pyridine in 100 cc dioxane to which 4 cc acetic acid have been added. The reaction mixture is then immediately filtered, yielding 6 g of the desired indamine, as monoacetate thereof. The product is practically pure and melts with decomposition between 125° and 128°.

Molecular weight calculated for $C_{16}H_{21}N_5O_3$ ... 331
Molecular weight found by potentiometric measurement effected with perchloric acid in acetic medium ... 340

| Analysis | Calculated for $C_{16}H_{21}N_5O_3$ | Found | |
|---|---|---|---|
| C% | 58.00 | 56.97 | 56.85 |
| H% | 6.34 | 6.34 | 6.44 |
| N% | 21.14 | 20.86 | 20.98 |

EXAMPLE 3

N-[(4'-amino 2'-methoxy)phenyl] 3-amino 2-aza benzoquinone diimine persulfate is prepared as follows:

A first solution is prepared by dissolving 0.05 mole (6.9 g) methoxyparaphenylene diamine in a mixture of 50 cc acetone and 30 cc water. A second solution is prepared by dissolving 0.05 mole (5.45 g) 2,6-diaminopyridine in 50 cc acetone. The two solutions are mixed and allowed to cool. There is then added 25 cc ammonia (22° Be) and 50 cc hydrogen peroxide (40 volumes). After a few minutes, there are added sufficient acetic acid to adjust the pH 8 and 20 g ammonium persulfate dissolved in 40 cc ice water. The reaction mixture is then immediately filtered, yielding 8 g of the desired indamine, as the persulfate, the said product being chromatographically pure.

EXAMPLE 4

N-[(4'-amino 2'-methoxy)phenyl] 3-amino 2-aza benzoquinone diimine paratoluene sulfonate is prepared as follows:

The indamine persulfate (7 g) of Example 3 is treated with 100 cc of an aqueous solution of 10 cc ammonia (22° Be). The indamine that is released is immediately extracted, using a solution of methylisobutylketone. There is added to the extraction solvent paratoluene sulfonic acid in sufficient quantity to precipitate the indamine as paratoluene sulfonate. The resulting crystals are dried and washed, using methylisobutylketone. The product is chromatographically pure.

EXAMPLE 5

N-[(4'-amino 3'-chloro)phenyl] 3-amino 2-aza benzoquinone diimine persulfate is prepared as follows:

A first solution is prepared by dissolving 0.05 mole (7.1 g) chloroparaphenylene diamine in 100 cc acetone to which there has previously been added 40 cc water and 10 cc ammonia (22° Be). A second solution is prepared by dissolving 0.05 mole (5.45 g) 2,6-diaminopyridine in 25 cc acetone to which 10 cc water have been added. The two solutions are mixed and 25 cc ammonia (22° Be) are added, and then 70 cc hydrogen peroxide (40 volumes). The reaction mixture, which is allowed to stand for two hours at ambient temperature is then neutralized with acetic acid, cooled in an ice-salt mixture. To the thus cooled reaction mixture there are then added 20 g ammonium persulfate in solution in 50 cc water. The reaction mixture is then filtered, yielding 8 g of the desired indamine, as persulfate. This product is chromatographically pure.

EXAMPLE 6

N-[(4'-amino 3'-chloro)phenyl] 3-amino 2-aza benzoquinone diimine monoacetate is prepared as follows:

Six grams of the indamine persulfate obtained in Example 5 are treated with 80 cc of an aqueous solution of 8 cc ammonia (22° Be) and the freed indamine is immediately extracted, using methyl isobutylketone. Acetic acid in amounts sufficient to precipitate the indamine acetate is added to the extraction solvent. There is thus obtained, after filtering, 2.5 g of the chromatographically pure product which melts with decomposition between 134° and 136°.

Molecular weight calculated for $C_{11}H_{10}N_5Cl \cdot CH_3CO_2H$ ... 307
Molecular weight found by potentiometric measurement in acetic medium, using perchloric acid ... 315

| Analysis | Calculated for $C_{11}H_{10}N_5Cl \cdot CH_3CO_2H$ | Found | |
|---|---|---|---|
| C% | 50.73 | 49.15 | 49.35 |
| H% | 4.58 | 4.55 | 4.70 |
| N% | 22.76 | 22.29 | 22.30 |

EXAMPLE 7

N-[(4'-amino)phenyl] 3-amino 2-aza benzoquinone diimine monoacetate, monohydrate is prepared as follows:

There is first prepared, by a process identical to that described in Example 3 above, the persulfate of N-[(4'-amino)phenyl]-3-amino 2-aza benzoquinone diimine.

The crude persulfate (6 g) that is obtained is treated with 80 cc of an aqueous solution of 8 cc ammonia (22° Be) with immediate extraction of the freed indamine, using methylisobutylketone. Acetic acid in an amount sufficient to precipitate the desired indamine acetate is added to the extraction solvent. The reaction mixture is then immediately filtered, the resulting above product then being washed with acetone and dried on $P_2O_5$.

This product is chromatographically pure and melts with decomposition at 137°.

Molecular weight calculated for $C_{13}H_{17}N_5O_3$ ... 291
Molecular weight found by potentiometric measurement in acetic medium, using perchloric acid ... 304

| Analysis | Calculated for $C_{13}H_{17}N_5O_3$ | Found |
|---|---|---|
| C% | 53.60 | 52.76 |
| H% | 5.84 | 5.93 |
| N% | 24.05 | 23.76 |

EXAMPLE 8

N-[(4'-dimethylamino)phenyl] 3-amino 2-aza benzoquinone diimine hydrochloride is prepared as follows:

To a solution of 0.0254 mole (4.73 g) paranitrosodimethylaniline HCl in 50 cc water at 50° C, there is gradually added a solution of 0.0254 mole (2.77 g) 2,6-diaminopyridine in 50 cc water. The reaction mixture is held for 10 minutes at this temperature, and then for one hour at ambient temperature. The reaction mixture is then filtered, yielding 4 g of the above indamine as monohydrochloride. This product is then washed with ice water to remove any traces of the nitroso derivative of the starting material that it may contain. The product is chromatographically pure and melts with decomposition between 240° and 242°.

EXAMPLE 9

N-[(4'-dimethylamino)phenyl] 3-amino 2-aza benzoquinone diimine acetate is prepared as follows:

0.03 mole (8.31 g) of the indamine hydrochloride prepared as in Example 8 is treated by 200 cc of a normal sodium hydroxide solution, thereby releasing the indamine which is extracted with methylisobutylketone. 5 cc of acetic acid are immediately added to the extraction solvent. The reaction mixture is then filtered, yielding 4.2 g of N-[(4'-dimethylamino)phenyl] 3-amino 2-aza benzoquinone diimine acetate which melts with decomposition between 170° and 172°.

Molecular weight calculated for $C_{15}H_{19}N_5O_2$ ... 301
Molecular weight found by potentiometric measurement in acetic medium, using perchloric acid ... 287

| Analysis | Calculated for $C_{15}H_{19}N_5O_2$ | Found | |
|---|---|---|---|
| C% | 59.80 | 58.78 | 58.69 |
| H% | 6.31 | 6.30 | 6.28 |
| N% | 23.25 | 23.23 | 23.36 |

EXAMPLE 10

N-[(4'-dimethylamino)phenyl] 3-amino 2-aza benzoquinone diimine perchlorate is prepared as follows:

0.01 mole (2.09 g) N,N-dimethyl paraphenylene diamine dihydrochloride and 0.01 mole 2,6-diaminopyridine are dissolved in 20 cc water to which 5 cc ammonia (22° Be) have been added. There are gradually added, with agitation, 20 cc hydrogen peroxide (20 volumes). The reaction mixture is allowed to stand for 20 minutes at ambient temperature, 20 g sodium perchlorate are then added, with cooling to 0° C for three hours. The azaindamine perchlorate is then isolated by filtering, the product then being washed with a small amount of ice water and vacuum dried. The product is chromatographically pure and melts with decomposition at 210° C.

EXAMPLE 11

The double chloride of zinc and N-[(4'-ethyl-β-acetylaminoethyl amino)phenyl] 3-amino 2-aza benzoquinone diimine is prepared as follows:

To 40 cc absolute ethyl alcohol, there are added 0.01 mole (1.09 g) of 2,6-diaminopyridine, 0.01 mole para nitroso N,N-ethyl-β-acetylaminoethyl aniline (2.35 g) and 1.6 g anhydrous zinc chloride. The reaction mixture is heated to reflux for two hours. The double chloride of zinc and azaindamine is then isolated by filtering the reaction mixture and the product is washed with hot ethanol and dried under vacuum. 2.1 g of the chromatographically pure product is obtained.

EXAMPLE 12

The double chloride of zinc and N-[(4'-ethyl carbamylmethylamino)phenyl] 3-amino 2-aza benzoquinone diimine is prepared as follows:

To 40 cc absolute ethanol there are added 0.01 mole (1.09 g) of 2,6-diaminopyridine, 0.01 mole (2.07 g) paranitroso N,N-ethyl carbamylmethylaniline, and 1.6 g anhydrous zinc chloride.

The reaction mixture is heated under reflux for two hours. The resulting double chloride of zinc and azaindamine is then filtered from the reaction mixture washed with hot ethanol and vacuum dried. Two grams of the chromatographically pure product are obtained.

EXAMPLE 13

N-[(4'-di-β-hydroxyethylamino)phenyl] 3-amino 2-aza benzoquinone diimine hydrobromide is prepared as follows:

To 20 cc absolute ethyl alcohol there are added 0.0024 mole (0.7 g) paranitroso di-β-hydroxyethylaniline hydrobromide and 0.0024 mole (0.26 g) 2,6-diaminopyridine. The reaction mixture is heated, with agitation, for three quarters of an hour at 60° C. The resulting azaindamine hydrobromide is then filtered from the reaction mixture, washed with ethanol and vacuum dried. The product is chromatographically pure.

| Analysis | Calculated for $C_{15}H_{20}N_5O_2Br$ | Found | |
|---|---|---|---|
| C% | 47.12 | 46.98 | 46.86 |
| H% | 5.24 | 5.19 | 5.24 |
| N% | 18.32 | 18.31 | 18.57 |
| Br% | 20.92 | 20.87 | 20.68 |

EXAMPLE 14

The double chloride of zinc and N-[(4'-di-β-hydroxyethylamino)phenyl] 3-amino 2-aza benzoquinone diimine is prepared as follows:

There is heated under reflux for two hours, with agitation, a reaction mixture of 0.01 mole (1.09 g) 2,6-diaminopyridine, 0.01 mole (2.10 g) paranitroso di-β-hydroxyethylaniline and 1.6 g anhydrous zinc chloride in 25 cc absolute ethanol. After cooling, the double chloride of zinc and the desired azaindamine is filtered from the reaction mixture and washed with hot absolute ethanol. 2.4 g of the chromatographically pure product is obtained.

EXAMPLE 15

Preparation of N-[(4'-diethylamino)-2'-chlorophenyl]-3-amino-2-aza benzoquinone diimine of the formula

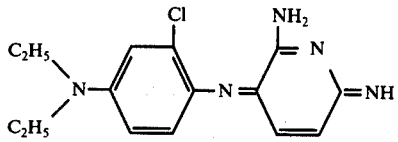

0.01 mole (2.71 g) of 2-chloro-4-N,N-diethylamino aniline and 0.01 mole (1.09 g) of 2,6-diaminopyridine are dissolved in 50 cc of a 50% hydroacetonic solution to which has been added 5 cc of ammonia (22° Be). To the resulting solution there is then added 0.03 mole (6.84 g) of ammonium persulfate in 25 cc of water.

The salt of the above indamine precipitates and it is then filtered and redissolved in 50 cc of boiling water. The resulting aqueous boiling solution is then alkalinized with 10 cc of ammonia (22° Be). After cooling, the above indamine precipitates and is then filtered, washed with water and dried under a vacuum. The product is chromatographically pure and melts at 175° C.

| Analysis | Calculated for $C_{16}H_{18}N_5Cl$ | Found | |
|---|---|---|---|
| C% | 60.86 | 60.75 | 60.60 |
| H% | 5.61 | 5.41 | 5.58 |
| N% | 22.20 | 22.00 | 22.37 |

EXAMPLE 16

Preparation of N-[(4'-ethyl-piperidinoethylamino)-phenyl]-3-amino-2-aza benzoquinone diimine dihydrochloride of the formula

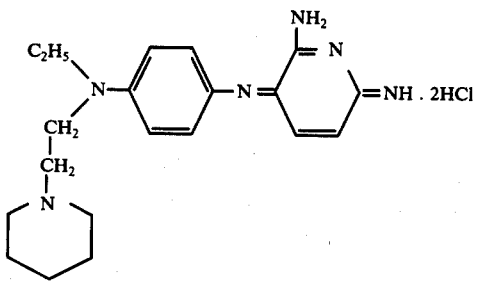

To 10 cc of water there are added 0.01 mole (1.09 g) of 2,6-diaminopyridine and 0.01 mole (3.34 g) of 4-nitroso-N-ethyl-N-β-piperidinoethyl aniline dihydrochloride.

The resulting mixture is heated with agitation for one hour at which point the mixture is then cooled to 0° C. The above azaindamine in the form of the dihydrochloride thereof crystallizes and is filtered therefrom. After recrystallization in ethanol and drying under a vacuum, the product melts with decomposition at 230° C.

| Analysis | Calculated for $C_{20}H_{30}N_6Cl_2$ | Found | |
|---|---|---|---|
| C% | 56.47 | 56.00 | 56.12 |
| H% | 7.05 | 6.94 | 6.82 |
| N% | 18.82 | 18.48 | 18.65 |

| Analysis | Calculated for $C_{20}H_{30}N_6Cl_2$ | Found | |
|---|---|---|---|
| Cl% | 16.71 | 16.49 | 16.57 |

EXAMPLE 17

The following dye composition is prepared:
Dye of Example 1 . . . 0.1 g
Water, q.s.p. . . . 100 g This composition when applied to 95% white hair for 20 minutes imparts thereto, after rinsing and shampooing, a Nile green shade.

EXAMPLE 18

The following dye composition is prepared:
Dye of Example 1 . . . 0.1 g
Water, q.s.p. . . . 100 g
Ammonia (22° Be), q.s.p. . . . pH 9

This composition, when applied to 95% white hair for three minutes, imparts thereto, after rinsing and shampooing, an elegant turquoise blue shade.

EXAMPLE 19

The following dye composition is prepared:
Dye of Example 1 . . . 0.1 g
Butyl glycol . . . 5 g
Hydroxyethylene lauryl alcohol (10.5 moles ethylene oxide) . . . 5 g
Water, q.s.p. . . . 100 g This composition, when applied to 95% white hair for 20 minutes, imparts thereto, after rinsing and shampooing, a greenish-blue shade.

EXAMPLE 20

The following dye composition is prepared:
Dye of Example 1 . . . 0.02 g
N-[(2',4'-diamino 5'-methoxy)phenyl] benzoquinone imine . . . 0.1 g
Nitrometaphenylene diamine . . . 0.02 g
Ammonia (22° Be), q.s.p. . . . pH 9
Water, q.s.p. . . . 100 g This composition, applied to 60% white hair for 20 minutes, imparts thereto, after rinsing and shampooing a dark green bronze coloration.

EXAMPLE 21

The following dye composition is prepared:
Dye of Example 1 . . . 0.02 g
N-[(2',4'-diamino 5'-methoxy)phenyl] benzoquinone imine . . . 0.1 g
Nitroparaphenylene diamine . . . 0.02 g
Ethyl alcohol (95°) . . . 10 g
Ammonia (22° Be), q.s.p. . . . pH 9
Water, q.s.p. . . . 100 g This composition, when applied to 60% white hair for 20 minutes, imparts thereto, after rinsing and shampooing, a moire chestnut shade with purple highlights.

EXAMPLE 22

The following dye composition is prepared:
Dye of Example 1 . . . 0.02 g
N-[(2',4'-diamino 5'-methoxy)phenyl] benzoquinone imine . . . 0.1 g
Ethyl alcohol (95°) . . . 10 g
Ammonia (22° Be), q.s.p. . . . pH 9
Water, q.s.p. . . . 100 g This composition, when applied to 60% white hair for 15 minutes, imparts thereto, after rinsing and shampooing, an ashy grey shade.

EXAMPLE 23

The following dye composition is prepared:
Dye of Example 1 . . . 0.2 g
Ammonia (22° Be), q.s.p. . . . pH 9
Water, q.s.p. . . . 100 g This composition when applied to dark brown hair for 20 minutes imparts thereto, after rinsing and shampooing, a raven black coloration.

EXAMPLE 24

The following dye composition is prepared:
Dye of Example 2 . . . 0.1 g.
Water, q.s.p. . . . 100 g This composition, when applied to 95% white hair for 20 minutes, imparts thereto, after rinsing and shampooing, a jade green shade.

EXAMPLE 25

The following dye composition is prepared:
Dye of Example 2 . . . 0.1 g
Water, q.s.p. . . . 100 g This composition, when applied to chestnut hair for 20 minutes, imparts thereto, after rinsing and shampooing, a brown hue with bronze highlights.

EXAMPLE 26

The following dye composition is prepared:
Dye of Example 2 . . . 0.04 g
N-[(2',4'-diamino 5'-methoxy)phenyl] benzoquinone imine . . . 0.15 g
Ethyl alcohol (95°) . . . 10 g
Water, q.s.p. . . . 100 g This composition, when applied to 60% white hair for 20 minutes, imparts thereto, after rinsing and shampooing, an ashy grey shade with light purple pearly highlights.

EXAMPLE 27

The following dye composition is prepared:
Dye of Example 1 . . . 0.02 g
N-[(2',4'-diamino 5'-methoxy)phenyl] benzoquinone imine . . . 0.1 g
Nitro orthophenylene diamine . . . 0.02 g
Ammonia (22° Be), q.s.p. . . . pH 9
Water, q.s.p. . . . 100 g This composition, when applied to 60% white hair for 20 minutes, imparts thereto, after rinsing and shampooing, a bronze chestnut shade.

EXAMPLE 28

The following dye composition is prepared:
Dye of Example 3 . . . 0.1 g
Ammonia (22° Be), q.s.p. . . . pH 8
Water, q.s.p. . . . 100 g This composition, when applied to 95% white hair for 20 minutes, imparts thereto, after rinsing and shampooing, an elegant greenish blue coloration.

EXAMPLE 29

The following dye composition is prepared:
Dye of Example 4 . . . 1 g
Ammonia (22° Be), q.s.p. . . . pH 9.5
Water, q.s.p. . . . 100 g This composition, when applied to 95% white hair for 10 minutes, imparts thereto, after rinsing and shampooing, a pale greenish blue shade.

EXAMPLE 30

The following hair setting lotion composition is prepared:
Dye of Example 1 . . . 0.012 g
Toluylene blue acetate . . . 0.012 g
Nitroparaphenylene diamine . . . 0.1 g
Copolymer of crotonic acid and vinyl acetate (M.W. 45,000 – 50,000, 10:90) . . . 2 g
Ethyl alcohol (96°), q.s.p. . . . 50°
Water, q.s.p. . . . 100 g This hair setting lotion, when applied to 100% white hair, imparts thereto a silvery medium grey shade.

EXAMPLE 31

The following hair setting lotion composition is prepared:
Dye of Example 1 . . . 0.006 g
Toluylene blue acetate . . . 0.012 g
Nitroparaphenylene diamine . . . 0.2 g
Copolymer of crotonic acid and vinyl acetate (M.W. 45,000 – 50,000, 10:90) . . . 2 g
Ethyl alcohol (96°), q.s.p. . . . 50°
Water, q.s.p. . . . 100 g This hair setting lotion, when applied on straw colored hair, imparts thereto a dark golden blond coloration.

EXAMPLE 32

The following hair setting lotion composition is prepared:
Dye of Example 1 . . . 0.01 g
N-[(2',4'-diamino 5'-methoxy) phenyl] 2-methyl 5-methoxy benzoquinone diimine acetate . . . 0.1 g
Copolymer of crotonic acid and vinyl acetate (M.W. 45,000 – 50,000, 10:90) . . . 2 g
Ethyl alcohol (96°), q.s.p. . . . 50°
Water, q.s.p. . . . 100 g This hair setting lotion, when applied to 100% white hair, imparts thereto a very intense ultramarine blue coloration.

EXAMPLE 33

The following hair setting lotion composition is prepared:
Dye of Example 2 . . . 0.05 g
Copolymer of crotonic acid and vinyl acetate (M.W. 45,000–50,000 10:90) . . . 2 g
Ethyl alcohol (96°), q.s.p. . . . 50°
Water, q.s.p. . . . 100 g This hair setting lotion, when applied to 100% white hair, imparts thereto a very intense and luminous greenish blue coloration.

EXAMPLE 34

The following dye composition is prepared:
Dye of Example 1 . . . 0.5 g
Water, q.s.p. . . . 100 g
Lactic acid, q.s.p. . . . pH 3.5

This composition, when applied to 95% white hair for 20 minutes, imparts thereto, after rinsing and shampooing, a pale green color.

EXAMPLE 35

The following dye composition is prepared:

Dye of Example 6 ... 0.1 g
Water, q.s.p. ... 100 g

This composition, when applied to 60% white hair for 10 minutes, imparts thereto, after rinsing and shampooing, a slate blue shade with silver highlights.

EXAMPLE 36

The following hair setting lotion composition is prepared:
Dye of Example 6 ... 0.1 g
Copolymer of crotonic acid and vinyl acetate (M.W. 45,000 – 50,000, 10:90) ... 2 g
Ethyl alcohol (96°), q.s.p. ... 50°
Water, q.s.p. ... 100 g This hair setting lotion, when applied to 100% white hair, imparts thereto an intense royal blue shade.

EXAMPLE 37

The following dye composition is prepared:
Dye of Example 5 ... 0.15 g
Water, q.s.p. ... 100 g
Ammonia (22° Be), q.s.p. ... pH 9

This composition, when applied to 95% white hair for 20 minutes, imparts thereto, after rinsing and shampooing, a light blue color.

EXAMPLE 38

The following dye composition is prepared:
Dye of Example 7 ... 0.05 g
Water, q.s.p. ... 100 g This composition, when applied to 95% white hair for 5 minutes, imparts thereto, after rinsing and shampooing, a very lightly green-tinted blue.

EXAMPLE 39

Dye of Example 8 ... 0.07 g
Copolymer of crotonic acid and vinyl acetate (M.W. 45,000–50,000, 10:90) ... 2 g
Ethyl alcohol (96°), q.s.p. ... 50°
Water, q.s.p. ... 100 g This hair setting lotion, when applied to 100% white hair, imparts thereto a very intense peacock blue.

EXAMPLE 40

The following hair setting lotion composition is prepared:
Dye of Example 13 ... 0.015 g
Copolymer of crotonic acid and vinyl acetate (M.W. 45,000 – 50,000, 10:90) ... 2 g
Ethyl alcohol (96°), q.s.p. ... 50°
Water, q.s.p. ... 100 g
Triethanolamine, q.s.p. ... pH 7

This hair setting lotion, when applied to 100% white hair, imparts thereto a light silvery blue.

EXAMPLE 41

The following hair setting lotion composition is prepared:
Dye of Example 14 ... 0.005 g
Copolymer of crotonic acid and vinyl acetate (M.W. 45,000 – 50,000, 10:90) ... 2 g
Ethyl alcohol (96°), q.s.p. ... 50°
Water, q.s.p. ... 100 g
Triethanolamine, q.s.p. ... pH 7

This hair setting lotion, when applied on bleached hair, imparts thereto a pronouncedly pearly pale green.

EXAMPLE 42

The following hair setting lotion composition is prepared:
Dye of Example 10 ... 0.1 g
Copolymer of crotonic acid and vinyl acetate (M.W. 45,000 – 50,000, 10:90) ... 2 g
Ethyl alcohol (96°), q.s.p. ... 50°
Water, q.s.p. ... 100 g
Triethanolamine, q.s.p. ... pH 7

This hair setting lotion, when applied to unbleached hair, imparts thereto a turquoise blue.

EXAMPLE 43

The following dye composition is prepared:
Dye of Example 10 ... 0.0025 g
Water, q.s.p. ... 100 g
Ammonia (22° Be), q.s.p. ... pH 10

This composition, when applied to bleached hair for two minutes at ambient temperature, imparts thereto, after rinsing and shampooing, a pearly appearance with pale green highlights.

EXAMPLE 44

The following hair setting lotion composition is prepared:
Dye of Example 11 ... 0.035 g
N-[(4'-amino)phenyl] 3-amino 6-methyl benzoquinone imine ... 0.05 g
Copolymer of vinyl acetate and crotonic acid (M.W. 45,000 – 50,000, 90:10) ... 2 g
Ethyl alcohol (96°), q.s.p. ... 50°
Water, q.s.p. ... 100 g
Triethanolamine, q.s.p. ... pH 7

This hair setting lotion, when applied to bleached hair, imparts thereto a pearly light violet color.

EXAMPLE 45

The following dye composition is prepared:
Dye of Example 12 ... 0.05 g
Water, q.s.p. ... 100 g
Ammonia (22° Be), q.s.p. ... pH 10

This composition, when applied to bleached hair for 20 minutes at ambient temperature, imparts thereto, after rinsing and shampooing, a pearly, pale emerald green shade.

EXAMPLE 46

The following dye solution is prepared:
Dye of Example 15 ... 0.05 g
Ethyl alcohol (96° titer) ... 40 g
Water, q.s.p. ... 100 g
Lactic acid, q.s.p. ... pH = 6.5

This composition, when applied to bleached hair for 20 minutes, after rinsing and shampooing, imparts thereto a very intense peacock blue coloration.

EXAMPLE 47

The following dye solution is prepared:
Dye of Example 16 ... 0.15 g
Ethyl alcohol (96° titer) ... 25 g
Ammonia (22° Be), q.s.p. ... pH = 9
Water, q.s.p. ... 100 g This composition, when applied to bleached hair for 20 minutes, imparts thereto, after rinsing and shampooing, a very luminous and intense blue coloration.

EXAMPLE 48

The following hair setting lotion is prepared:
Dye of Example 9 ... 0.012 g
4,4′-dihydroxy-2-amino azobenzene ... 0.02 g
N-[(4′-amino-3′-methyl)phenyl]2,6-dimethyl-3-acetamino benzoquinone imine ... 0.01 g
N-[(4′-hydroxy-2′-chloro)phenyl]-2-methyl-5-ureido benzoquinone imine ... 0.01 g
Gantrez ES 435 (butyl monoester of methylvinyl ether/maleic anhydride copolymer ... 3 g
Ethanol (96°) ... 50 g
Ammonia, q.s.p. ... pH = 8.5
Water, q.s.p. ... 100 g This hair setting lotion when applied to bleached hair imparts thereto after drying a bright pistachio green coloration.

This same hair setting lotion when applied to gray hair under the same conditions imparts thereto an iridescent almond green coloration.

EXAMPLE 49

The following hair setting lotion is prepared:
Dye of Example 13 ... 0.02 g
Meldolas Blue (oxazinic dye sold by Francolor) ... 0.03 g
Polyvinylpyrrolidone K30-Mol. Wt = 40,000, viscosity = 2.4 cp in a 5% aqueous solution at 25° C ... 2.5 g
Isopropyl alcohol ... 35 g
Ammonia, q.s.p. ... pH = 7
Water, q.s.p. ... 100 g This hair setting lotion when applied to white hair imparts thereto after drying a steel blue coloration.

EXAMPLE 50

The following hair setting lotion is prepared:
Dye of Example 12 ... 0.012 g
1,4-di-($\beta$-morpholino ethyl) amino anthraquinone ... 0.1 g
Copolymer of polyvinylpyrrolidone and vinyl acetate (70/30, M.W. = 40,000) ... 1.5 g
Isopropyl alcohol ... 20 g
Ammonia, q.s.p. ... pH = 10
Water, q.s.p. ... 100 g This hair setting lotion when applied to natural gray hair imparts thereto, after drying, an ocean green coloration.

EXAMPLE 51

The following hair setting lotion composition is prepared:
Dye of Example 14 ... 0.006 g
2,4,6-trihydroxy azobenzene ... 0.01 g
Bis-methyl [1,5-(anthraquinonylamino ethyl)methyl morpholinium] sulfate ... 0.02 g
Copolymer of polyvinylpyrrolidone and vinyl acetate (60/40, M.W. = 50,000 ... 2 g
Ethanol, 96° titer ... 30 g
Ammonia, q.s.p. ... pH = 6
Water, q.s.p. ... 100 g This hair setting lotion when applied to gray hair imparts thereto, after drying, an orange gray coloration.

EXAMPLE 52

The following hair setting lotion composition is prepared:
Dye of Example 9 ... 0.01 g
N-[(4′-amino)phenyl]-3-ureido benzoquinone imine ... 0.01 g
N-[(4′-hydroxy)phenyl]-2-methyl-5-acetylamino benzoquinone imine ... 0.01 g
Copolymer of polyvinylpyrrolidone and vinyl acetate (30/70, M.W. = 160,000) ... 1 g
Ethanol, 96° titer ... 30 g
Acetic acid, q.s.p. ... pH = 5
Water, q.s.p. ... 100 g This hair setting lotion when applied to bleached hair imparts thereto, after drying, an intense turquoise blue coloration.

EXAMPLE 53

The following dye composition in gel form is prepared:
Dye of Example 13 ... 0.1 g
N-[(2′-chloro-4′-hydroxy)]2-phenyl methyl-5-ureido benzoquinone imine ... 0.05 g
N-[4′-amino)phenyl[-3-ureido benzoquinone imine ... 0.05 g
Nonyl phenol oxyethylenated with 9 moles of ethylene oxide ... 12.5 g
Diethanolamide of the fatty acids of coco and coprah ... 6.25 g
Butyl glycol ... 3 g
Propylene glycol ... 8 g
Ammonia, q.s.p. ... pH = 9.5
Water, q.s.p. ... 100 g This composition is applied to gray hair for 20 minutes at ambient temperature. Thereafter the hair is rinsed, shampooed, rinsed again and dried. The resulting color of the hair is an intense blue green coloration.

The same composition when applied to previously bleached hair, under the same conditions, imparts thereto a very lively blue coloration.

What is claimed is:

1. An indamine selected from the group consisting of
a. an indamine having the formula

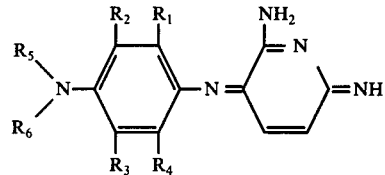

wherein $R_1$, $R_2$, $R_3$ and $R_4$ each independently are selected from the group consisting of hydrogen, halogen, lower alkyl having 1-4 carbon atoms and lower alkoxy having 1-4 carbon atoms, and $R_5$ and $R_6$ are selected from the group consisting of hydrogen, lower alkyl having 1-4 carbon atoms and lower alkyl having 1-4 carbon atoms and substituted with a member selected from the group consisting of acetylamino and carbamyl with at least one of $R_5$ and $R_6$ being said lower alkyl substituted with acetylamino or carbamyl,
b. a human hair compatible water soluble acid salt of said indamine in (a), and
c. a double chloride of zinc and said indamine in (a).

2. The indamine of claim 1 wherein said human hair compatible water soluble salt of said indamine in (a) is a salt selected from the group consisting of acetate, tartrate, paratoluene sulfonate, hydrochloride, hydrobromide, persulfate and perchlorate.

3. The indamine of claim 1 in the form of a double chloride of zinc and said indamine in (a).

4. The indamine of claim 1 which is the double chloride of zinc and N-[(4'-ethyl-β-acetylamino-ethyl amino) phenyl]-3-amino-2-aza benzoquinone diimine.

5. The indamine of claim 1 which is the double chloride of zinc and N-[(4'-ethyl carbamylmethylamino)-phenyl]3-amino-2-aza benzoquinone diimine.

* * * * *